United States Patent
Cavalli et al.

[11] Patent Number: 5,905,054
[45] Date of Patent: *May 18, 1999

[54] CATALYSTS FOR THE OXICHLORINATION OF ETHYLENE, METHOD FOR PREPARING THEM, AND OXICHLORINATION METHOD USING THE SAME

[75] Inventors: Luigi Cavalli, Novara; Carlo Rubini, San Fermo della Battaglia, both of Italy

[73] Assignee: Montecatini Tecnologie S.r.l., Italy

[*] Notice: This patent is subject to a terminal disclaimer.

[21] Appl. No.: 08/751,812

[22] Filed: Nov. 19, 1996

[30] Foreign Application Priority Data

Nov. 21, 1995 [IT] Italy .................... MI95A2396

[51] Int. Cl.$^6$ .................... B01J 35/10; B01J 37/00; B01J 23/28; C07C 17/154
[52] U.S. Cl. .................... 502/225; 570/245
[58] Field of Search .................... 502/225; 570/245

[56] References Cited

U.S. PATENT DOCUMENTS 4,441,990  4/1984  Huang .................... 208/111
5,166,120  11/1992  Deller et al. .................... 502/225
5,330,958  7/1994  Viola et al. .................... 502/316

FOREIGN PATENT DOCUMENTS 0 461 431  12/1991  European Pat. Off. .
0 678 331  10/1995  European Pat. Off. .
0 732 146  9/1996  European Pat. Off. .

OTHER PUBLICATIONS

Ullmann's Encyclopedia of Industrial Chemistry, Fifth Edition, vol. A6, 1986 pp. 266–267 XP002025505.

Kirk Othmer Encyclopedia of Chemical Technology, Third Edition, vol. 5, 1989, pp. 726–727, XP002025506.

*Primary Examiner*—Alan L. Rotman
*Attorney, Agent, or Firm*—Bryan Cave LLP

[57] ABSTRACT

Catalysts for the oxichlorination of ethylene to 1,2-dichlorethane, comprising copper chloride as a main component, in the form of hollow cylindrical granules having at least three through holes, obtained by compression forming by using, for lubrication, a lubricant placed on the walls of the forming chamber and on the plungers of the mold.

13 Claims, No Drawings

CATALYSTS FOR THE OXICHLORINATION OF ETHYLENE, METHOD FOR PREPARING THEM, AND OXICHLORINATION METHOD USING THE SAME

The present invention relates to granular catalysts for the fixed-bed oxichlorination of ethylene into 1,2-dichlorethane, obtained with a particular compression forming method (tableting).

It relates in particular to a catalyst that comprises copper chloride ($CuCl_2$) as an active component supported on alumina.

These catalysts have a very narrow porosity distribution. Due to the high surface-to-volume ratio that the granules of said catalysts allow to provide, and to the porosity characteristics of the granule, these catalysts allow to considerably reduce the load losses that occur in fixed-bed reactors and to significantly improve the activity and selectivity of the catalyst.

BACKGROUND OF THE INVENTION

A prior application in the name of the same Applicant, which is still pending, describes catalysts and supports for catalysts having a specific geometric shape, for example a cylindrical shape with through holes, with a circular or multilobed cross-section, obtained by tableting powders by using an external lubricant that is applied to the surface of the forming chamber and on the plungers of the mold instead of being dispersed in the bulk of the powder to be tableted.

The application does not describe catalysts for the oxichlorination of ethylene into 1,2-dichlorethane.

The synthesis of 1,2-dichlorethane by oxichlorination of ethylene can be performed, as known, in a fluidized-bed reactor or in a fixed-bed reactor. In the first case more uniform distribution of the temperature in the reactor is obtained (by avoiding localized overheating), with the detriment of some difficulty in fluidization, caused by the tendency of the catalyst particles to stick. In the second case, management of reaction parameters is easier, but due to the low heat exchange coefficient among the catalyst granules and between said granules and the reaction gas, localized temperature increases, known as "hot spots", can occur. These localized temperature increases must be avoided for reasons linked to the selectivity and useful life of the catalyst.

A first attempt to solve the problem of heat exchange among the granules of catalyst for the oxichlorination of ethylene has resorted to ring-shaped granules or to circular and cylindrical granules having a given height-to-diameter ratio.

The problem of the heat exchange coefficient is not the only technical problem to be solved in the case of an efficient synthesis of 1,2-dichlorethane in a fixed-bed reactor.

In fact, the following characteristics are also requested to a granular catalyst used in the fixed-bed oxichlorination of ethylene:

low resistance to the gas flow (low load loss for an equal thickness of the catalyst bed);

a high effective surface, that is to say, a high surface-to-volume ratio; and good mechanical strength, in order to prevent breakage of the catalytic particles and consequent packing of the bed.

The catalysts that are normally used in the fixed-bed oxidative chlorination process (which are shaped like spheres, solid cylinders, or rings of various sizes) do not solve these problems satisfactorily. Moreover, when using these known configurations, diffusion of the reaction gases inside the granules of catalyst and complementary diffusion of the products from the inside of the granules are often very limited. This means that since the oxichlorinatlon reaction occurs more easily and selectively on the outer surface of the granule in the heterogeneous system taken into consideration, oxichlorination catalysts having known shapes are not used efficiently. Therefore, a large amount of catalyst has to be used in order to achieve the desired conversion, and thus tubes of adequate height have to be used in the case of tube-bundle fixed beds. With oxichlorination catalysts having known shapes, this entails a further increase in load losses, also because the empty spaces between the catalyst granules are small.

Catalysts having a shape other than the conventional ones are described in U.S. Pat. No. 4,441,990, which relates to tubular extruded granules that have an essentially triangular or quadrangular multilobed cross-section. These catalysts provided advantages in terms of resistance to breakage and pressure drop, but the results are not really very much different from those that can be obtained with conventional catalysts.

Extrusion is the process adopted industrially to form catalysts.

This process is technologically very simple to perform; however, it has the drawback that it is absolutely unsuitable for forming complex shapes that can offer a satisfactory solution to the above mentioned problems.

BRIEF DESCRIPTION OF THE INVENTION

The catalysts according to the invention are obtained by means of a compression-forming method known as tableting, in which the lubricant is not dispersed in the mass of powder to be formed (bulk lubrication) but is applied to the walls of the forming chamber and to the plungers of the mold (external lubrication).

Catalysts produced with this method have a higher porosity and narrower pore radius distribution than those prepared with bulk lubrication. Over 40% of the volume of the pores has a radius that corresponds to the peak value of the porosity distribution curve. Porosity is generally between 0.20 and 0.5 $cm^3/g$ (determined by mercury absorption). The surface area is generally between 80 and 180 $m^2/g$ (BET method).

The catalysts furthermore have constant size parameters. Constancy of these parameters is instead unobtainable with forming processes that use bulk lubrication, owing to the considerable sintering that deforms part or all of the catalyst particle.

Because of these deformations, the forming process that uses bulk lubrication cannot be used in industrial practice to produce granules having a complex geometric shape.

DESCRIPTION OF THE PREFERRED EMBODIMENTS

Preferred oxichlorination catalysts are prepared by supporting copper chloride and an alkaline or alkaline-earth halide (preferably potassium chloride and magnesium chloride) on alumina granules having the desired geometric shape.

The alumina support is obtained by forming, by means of the process according to the invention, alumina in the bohemite form and by then subjecting the granules to calcination at a temperature between 400° and 700° C. The granules are finally impregnated with an aqueous solution of copper chloride and potassium chloride. The following is a representative composition by weight of the catalyst:

$Al_2O_3$=80%; $CuCl_2$=15%; KCl=5%

The bohemite alumina that is used has a porosity that can vary within wide limits, for example between 0.5 and 1.9 cm$^3$/g. Over 40% of the volume of the pores of catalysts obtained from bohemite have a radius of 60–70 A. The surface area is between 80 and 380 m$^2$/g.

The lubricants that can be used to prepare the catalysts according to the invention include solids and liquids that are suitable for reducing the friction coefficient between the powder to be tabletted and the parts of the tabletter that make contact with said powder.

Examples of suitable lubricants are stearic acid and palmitic acid; alkaline and alkaline-earth salts of these acids, such as magnesium, potassium, or aluminum stearate; carbon black, talc, mono- and triglycerides such as glycerol monostearate and glycerol mono-oleate, paraffin oil, and perfluoropolyethers.

The liquid lubricants can be used as solutions or as dispersions in dispersants.

The amount of liquid lubricant is generally between 0.025 and 25 mg per granule.

The solid lubricants can be applied by dusting the forming chamber an the plungers, that is to say, by covering them with a thin layer of lubricant powder conveyed continuously by a stream of air.

The forming chamber and the plungers can be made of, or coated with, self-lubricating materials, such as polytetrafluoroethylene or ceramic material. This allows to avoid or reduce the use of lubricant.

The catalysts according to the invention have at least three through holes whose axes are preferably substantially parallel to each other and to the axis of the granule and are substantially mutually equidistant.

Preferably, the through holes have a circular cross-section and have axes which, relative to the cross-section of the particle, form the corners of a substantially equilateral triangle; said corners are orientated toward the points where the cross-section makes contact with the circumscribed circumference. In the preferred embodiment of the invention, the granules have cylindrical-circular lobes that are identical to each other and are coaxial to the through holes.

By virtue of these characteristics, in view of the particular geometric shape of the granules, it is possible to promote a high level of turbulence of the reaction gas on said granules in the operating conditions normally used in fixed-bed reactors for the oxichlorination of ethylene. Since said granules have a large free section, they offer less resistance to the gas flow, with consequent lower load losses. Furthermore, the fact of having a low equivalent diameter (where the equivalent diameter is the value 6×volume/total area) means having a larger effective surface, that is to say, a high surface-to-volume ratio. This entails better contact of the reaction gases with the surface of the catalyst, facilitating the conversion of the reagents and limiting internal diffusion phenomena, with a consequent increase in the selectivity of the oxichlorination reaction. With the catalyst according to the present invention high yields of 1,2-dichlorethane are obtained by using a lower amount of catalyst per unit volume than catalysts having known shapes.

The catalyst granule may also have a substantially triangular transverse cross-section with rounded corners.

The ratio between the pitch of the holes (that is to say, the distance between their respective axes) and the diameter of said holes is preferably between 1.15 and 1.5 and more preferably between 1.3 and 1.4.

The ratio between the height of the particle and the pitch of the holes is preferably between 1.5 and 2.5 and more preferably between 1.7 and 2.3.

In the case of catalysts having a circular cross-section, the ratio between the radius of curvature of each lobe and the pitch of the holes is preferably between 0.6 and 0.9, more preferably between 0.7 and 0.8. The ratio between the radius of curvature of the lobes and the radius of the through holes is preferably between 1.3 and 2.7, more preferably between 1.8 and 2.10. The ratio between the radius of the circle circumscribed about the cross-section and the radius of curvature of the circular lobes is preferably between 1.6 and 2, more preferably between 1.7 and 1.85. The surface-to-volume ratio of each granule in the multilobed version is preferably higher than 2.0 and more preferably higher than 2.2.

In the case of catalysts having a triangular transverse cross-section, the ratio between the radius of curvature of each rounded corner and the pitch of the holes is preferably between 0.6 and 0.9 and more preferably between 0.7 and 0.8. The ratio between the radius of the circle circumscribed about the cross-section and the radius of curvature of each rounded corner is preferably between 1.6 and 2, more preferably between 1.7 and 1.85. The surface-to-volume ratio of each granule, in the version having a triangular section, is preferably higher than 2.0, more preferably higher than 2.2.

The following examples are given by way of non-limitative illustration of the invention.

EXAMPLE 1

Bohemite alumina in powder form, having a surface area of 270 m$^2$/g and a pore volume of 0.5 cm$^3$/g, is tableted so as to form three-lobed cylindrical bodies that have through holes at each one of the three lobes. Cylinder height was 5 mm; hole diameter was 1.7 mm; the maximum size of the cross-section was 5.7 mm; and the average total surface area per granule was 202 mm$^2$.

The walls of the forming chamber and the plungers used to form the through holes were covered with a thin layer of stearic acid carried by a continuous stream of air.

The three-lobed granules were subjected to calcination at 550° C. for 3 hours and then impregnated with an aqueous solution containing copper chloride and potassium chloride in such an amount as to provide the following composition by weight of the catalyst: $CuCl_2$=15%; K=5%; $Al_2O_3$=80%.

After impregnation, the granules were subjected to drying at 150° C. for 3 hours.

The resulting catalyst granules had a surface area (BET) of 92 m$^2$/g and a porosity of 0.28 cm$^3$/g (mercury porosimeter). Pore volume distribution was such that over 40% of said pores had a radius of 60–70 A. The axial breaking strain was 68 kg/particle.

In order to determine activity, yield, selectivity, and pressure loss, the catalyst was loaded into a nickel tubular reactor having an internal diameter of 26.6 mm and a height of 1300 mm, placed in a thermostat-controlled bath of silicone oil.

The loading profile, from the top downward, was the following:

a first layer, 400 mm thick, constituted by mixed catalyst and graphite in the form of extruded cylindrical bodies measuring 5×5 mm, with a 1:1 catalyst/diluent volume ratio;

a second layer, 400 mm thick, constituted by catalyst granules.

A gas stream was fed downward from above at the following rate:

| | |
|---|---|
| ethylene | 21.6 Nl/h |
| HCl | 40 Nl/h |
| air | 57 Nl/h |

The temperature of the thermostat-controlled bath was kept at such a value as to ensure HCl conversion of 99%.

The pressure at the outlet of the reactor was 1 atmosphere and the pressure at the inlet of the reactor was compensated for by taking into account the pressure drop across the reactor.

The reaction products were cooled (quenched). The liquid fraction was analyzed by gas chromatography by using a Hewlett-Packard chromatograph provided with a capillary column for separating 1,2-dichlorethane, chloral, ethyl chloride, and other chlorinated by-products. The gaseous fraction was analyzed by using a Carlo Erba Fractovap gas chromatograph, provided with columns suitable for separating ethylene, CO, $CO_2$, $O_2$ and $N_2$.

With a temperature of 200° C provided by a thermostat-controlled bath, the selectivity of the conversion to 1,2-dichlorethane was 99% molar; ethyl chloride forming was 0.15% molar and chloral forming was 0.15% molar.

Pressure drop was 3.5 mm $H_2O$.

Comparison Example

Preparation of the catalyst of Example 1 was repeated, but the three-lobed cylindrical granules of alumina were instead obtained by using 3% by weight of stearic acid dispersed in the alumina powder to be tableted.

The resulting catalyst had a surface area of 107 $m^2/g$ and a porosity of 0.31 $cm^3/g$ with a rather wide distribution of the pore volume (70% of the pore volume having a radius spread between 50 and 200 A).

Catalytic selectivity determined in the conditions of Example 1 was 98% molar; forming of ethyl chloride was 0.2% molar and chloride forming was 0.15% molar.

What is claimed is:

1. A supported catalyst for the oxichlorination of ethylene to 1,2-dichloroethane, comprising copper chloride as active component, in the form of hollow cylindrical granules having at least three through holes, the copper chloride being supported on the granules, and the granules comprising alumina wherein the granules are obtained by a process comprising the compression forming of alumina with a surface area between 80 and 380 $m^2/g$ by using a lubricant placed on the walls of the forming chamber and on the plungers of the mold and wherein at least 40% of the volume of the pores has a radius that corresponds to the value of the peak of the porosity distribution curve.

2. A catalyst according to claim 1, having a surface area between 80 and 180 $m^2/g$.

3. A catalyst according to claim 2, wherein over 40% of the pore volume has a radius of 60–70 A.

4. A catalyst according to claim 1, wherein the through holes are substantially parallel to each other and to the axis of the granule.

5. A catalyst according to claim 4, wherein the through holes have a circular cross-section with axes which, in the granule cross-section, form corners of a substantially equilateral triangle.

6. A catalyst according to claim 4, wherein the ratio between the surface and the volume of the granules is higher than 2.

7. A catalyst according to claim 4, wherein the ratio between the radius of curvature of the lobes and the radius of the through holes is between 1.3 and 2.7.

8. A catalyst according to claim 4, wherein the ratio between the height of the granule and the pitch of the pores, intended as the distance between the respective axes, is between 1.5 and 2.5.

9. A catalyst according to claim 5, wherein their axial breaking strain is higher than 65 kg per particle.

10. A supported catalyst for the oxichlorination of ethylene to 1,2-dichloroethane, obtained with a process comprising the compression forming of alumina by using a lubricant placed on the walls of the forming chamber and on the plungers of the mold, and the subsequent impregnation, after calcination at 400–700° C., with an aqueous solution of copper chloride and of a chloride of an alkaline or alkaline-earth metal, wherein the supported catalysts comprise copper chloride as active component, in the form of hollow cylindrical granules having at least three through holes, the copper chloride being supported on the granules, and the granules comprise alumina, and wherein at least 40% of the value of the pores has a radius that corresponds to the value of the peak of the porosity distribution curve, said supported catalysts are obtained.

11. Method for preparing a catalyst for the oxichlorination of ethylene to 1,2-dichlorethane, comprising copper chloride as an active component, in the form of hollow cylindrical granules that have at least three through holes, wherein the granules of the catalysts and of the support for the catalyst are prepared by compression forming by using, for lubrication, a lubricant that is placed on the walls of the forming chamber and on the plungers of the mold.

12. Method for the oxichlorination of ethylene into 1,2-dichlorethane on a fixed bed, wherein the fixed bed comprises a catalyst as defined in claim 1.

13. Method for the oxichlorination of ethylene into 1,2-dichlorethane on a fixed bed, wherein the fixed bed comprises a catalyst obtained according to the method according to claim 11.

* * * * *